United States Patent [19]

Fuisz

[11] Patent Number: 5,422,136
[45] Date of Patent: * Jun. 6, 1995

[54] STARCH-BASED FOOD ENHANCING INGREDIENT

[75] Inventor: Richard C. Fuisz, Great Falls, Va.

[73] Assignee: Fuisz Technologies Ltd., Chantilly, Va.

[*] Notice: The portion of the term of this patent subsequent to Feb. 15, 2011 has been disclaimed.

[21] Appl. No.: 71,176

[22] Filed: Jun. 2, 1993

Related U.S. Application Data

[63] Continuation-in-part of Ser. No. 851,650, Mar. 16, 1992, Pat. No. 5,236,734, and Ser. No. 847,595, Mar. 5, 1992, Pat. No. 5,387,431, which is a continuation-in-part of Ser. No. 782,430, Oct. 25, 1991, abandoned, said Ser. No. 851,650, is a continuation-in-part of Ser. No. 602,485, Oct. 24, 1990, Pat. No. 5,096,492, which is a continuation-in-part of Ser. No. 169,838, Mar. 18, 1988, Pat. No. 4,855,326, which is a continuation-in-part of Ser. No. 40,371, Apr. 20, 1987, abandoned.

[51] Int. Cl.$^6$ .................... A23L 1/0522; A23L 1/314
[52] U.S. Cl. ..................................... 426/658; 426/661
[58] Field of Search ......................... 426/574, 658, 661

[56] References Cited

U.S. PATENT DOCUMENTS 5,286,513   2/1994   Fuisz ................................ 426/641

Primary Examiner—Arthur L. Corbin
Attorney, Agent, or Firm—Hoffmann & Baron

[57] ABSTRACT

A food enhancing ingredient is disclosed which comprises a matrix formed by subjecting a carrier material to flash-flow processing. A waxy starch is mixed with the matrix after the flash-flow processing or with the carrier material before the flash-flow processing. Preferably the food enhancing ingredient includes protein material.

28 Claims, 1 Drawing Sheet

STARCH-BASED FOOD ENHANCING INGREDIENT

BACKGROUND OF THE INVENTION

This application is a continuation-part of U.S. application Ser. No. 851,650 filed Mar. 16, 1992, now U.S. Pat. No. 5,236,734, which is a continuation-in-part of U.S. Ser. No. 602,485 filed Oct. 24, 1990, now U.S. Pat. No. 5,096,492, which, in turn, is a continuation-in-part of U.S. Ser. No. 169,838 filed Mar. 18, 1988, now U.S. Pat. No. 4,855,326, which in turn is a continuation-in-part of U.S. patent application Ser. No. 040,371, filed Apr. 20, 1987, now abandoned. This is also a continuation-in-part application of U.S. application Ser. No. 847,595 filed Mar. 5, 1992, now U.S. Pat. No. 5,387,431 which is a continuation-in-part application of U.S. application Ser. No. 782,430 filed Oct. 25, 1991, now abandoned. The disclosures of the '326 and '492 patents are incorporated herein by reference.

The present invention relates to a new method and product for enhancing food products, and, in particular, to the use of starch and starch-based ingredients.

Food technology in recent years has focused on providing high quality food products which are low in calorie content and low in cost. To this end, ingredients are constantly being sought for their versatility and compatibility with major food products.

Carbohydrates have always been a major component of the human diet. Sugars, for example, have been used extensively as a food ingredient. Materials containing both simple sugars and polymers of saccharides have also been used as ingredients in food products.

Starch is a carbohydrate which is a homopolymer of glucopyranoside. It is a polysaccharide found in many plant cells, and it consists of two (2) fractions: amylose or α-amylose, a straight chain of 1, 4, α-glucopyranose units, and amylopectin or β-amylose, a 1,6, α-branched form. The length of amylose chains averages between 500 and 2,000 glucose units, and is found in amounts of up to about 32% in grains and potatoes.

The present inventor, Dr. Fuisz, has discovered that processing sugars under flash-flow conditions alters the structure and behavior of the products during use. The processed sugars can be used for various purposes.

In U.S. Pat. No. 5,011,532, oleaginous substances, such as vegetable oil, mineral oil, baby oil, margarine, lanolin, cocoa butter and the like are disclosed as characteristically lacking affinity for water. The '532 patent explains how this characteristic is altered by mixing the oleaginous substance with sugar and subjecting the mixture to a type of flash-flow processing in a cotton candy spinning machine or the equivalent. As so modified, the products disperse in water forming a colloidal or pseudo-colloidal dispersion. Such modification enabled such widely disparate procedures as: (a) incorporating shortening oil in a cake mix containing flour but no egg to which water is added to produce a batter; and (b) producing a confection or medicated lozenge by dehydrating the dispersion and allowing the melted residue to solidify. The disclosure of the '532 patent is incorporated herein by reference.

Other disclosures dealing with substances processed with one or more sugars under flash-flow conditions will be found in U.S. Pat. Nos. 4,873,085; 4,997,586; 5,028,632 and 5,034,421.

More recently, Dr. Fuisz has discovered unexpected phenomena regarding maltodextrins. Maltodextrins contain a mix of sugars and polysaccharides which range from long-chain oligomers resulting from starch hydrolysis to sugars having a low number of monomeric units. Under FDA guidelines maltodextrin consists of nonsweet, nutritive saccharide polymers having a D.E. of less than 20, while corn syrup solids is regarded by the FDA as having a D.E. greater than 20. However, maltodextrins are referred to herein collectively as saccharide-based material consisting of nonsweet, nutritive saccharide polymers and other oligomers having six-carbon monomer units which collectively provide a carrier material capable of forming a matrix from flash-flow processing. In one parent case, U.S. application Ser. No. 847,595, now U.S. Pat. No. 5,387,431, maltodextrins were subjected to flash flow conditions and found to possess an unpredictably altered structure which can be used to enhance delivery of oleaginous material and active ingredients.

In U.S. Pat. No. 5,236,734 parent application Ser. No. 851,650, a new protein-based food product is disclosed which includes a carrier and an oleaginous substance. The carrier is preferably a saccharide or a cellulosic material. An acceptable ground meat product can be prepared in accordance with the invention set forth in the '734 patent. Other protein products, such as a soyburger, can be prepared in accordance with the '734 patent with acceptable results.

Other attempts to reduce fat in ground meat products include the use of a modified food starch, e.g., LEAN-BIND TM (a product of the National Starch and Chemical Company of Bridgewater, N.J.), which has an amylose content of less than 20%, in beef patties to reduce the fat content. This combination has been found, however, to produce only moderate success. The product prepared with the modified food starch is not even comparable to the higher fat content product.

In order, therefore, to entice the consumer to choose healthier food products as alternative, it is an object of the present invention to overcome the shortcomings known in the art of reduced fat products and food enhancement ingredients.

Other and further objects of the present invention will become apparent in the following description and its scope will be pointed out with the appended claims.

SUMMARY OF THE INVENTION

The present invention is a food enhancing ingredient and food products which incorporate the use of a matrix formed by subjecting a carrier material to flash-flow processing and a starch mixed with the matrix. In another embodiment, the starch can be combined with the carrier material prior to being subjected to flash-flow processing. Preferably, the matrix is in the form of a flake which exhibits bactericidal effects.

The primary ingredients in the compositions of the present invention include a matrix formed by subjecting the carrier material to flash-flow processing, and a starch. The starch can be mixed with the matrix or it can be combined with the carrier prior to being flash-flow processed into the matrix material.

Other ingredients which can be included in the compositions of the present invention include an oleaginous substance, oleoresins, spices, and flavor oils.

The carrier material can be selected from saccharides, cellulosics and mixtures thereof. When the carrier material is a maltodextrin, it is preferably a deionized maltodextrin.

The starch material can be modified starch or unmodified starch. In one preferred embodiment, the starch is a waxy starch which means that it has an amylose content of not greater than about 20%, the balance of the material being substantially amylopectin.

Finally, the compositions of the present invention are particularly useful in protein-based food products, and, in particular, as a fat replacement in protein based food products.

When starch is combined with a matrix material to form an ingredient for inclusion in a protein based food product, the amount of starch should not exceed 35% of the combination, and preferably does not exceed 25% of the combination. If starch is combined with a carrier prior to forming a matrix, it should be included in an amount not greater than 35%, and preferably not greater than 25% of the combined feedstock which is flash-flow processed to form the matrix.

Furthermore, the final product should contain no more than 1% starch, preferably no more than 0.75% starch, and most preferably not more than 0.5% starch by weight. Thus, the total starch content in and out of the matrix should not exceed 1.0%, 0.75%, or, 0.5%, respectively, for the preferred embodiments.

The food enhancing ingredient of the present invention provides a safe, expedient means of bulking a comestible while retaining cohesiveness and texture and moisture. It is ideal as a replacement for fat or other ingredients which noticeably reduce the bulk of the comestible when removed. It is particularly useful in protein based food products in which fat is an important ingredient for cohesiveness, bulk, moisture and texture.

The present invention further provides a means by which a starch can be successfully used as a fat replacement in products especially protein based products.

As a result of the present invention, various edible protein compositions can be provided which have enhanced taste, texture, and moisture, all without loss of bulk. This has been achieved by being able to include starch in a unique manner with a source of protein.

The present invention also enhances shelf life and reduces or inhibits microbial growth in food products.

Another advantage of the present invention is that high intensity flavorants such as oleoresins can be incorporated in bulk food products without incurring unwanted "hot spots" due to inadequate mixing, and thorough mixing can be achieved without deterioration of the food product.

In one particular aspect of the invention, a commercial scale manufacturing process and composition for reducing fat has been promoted without loss of product quality due to the reduction of fat in the product.

DETAILED DESCRIPTION OF THE INVENTION

Figure 1:
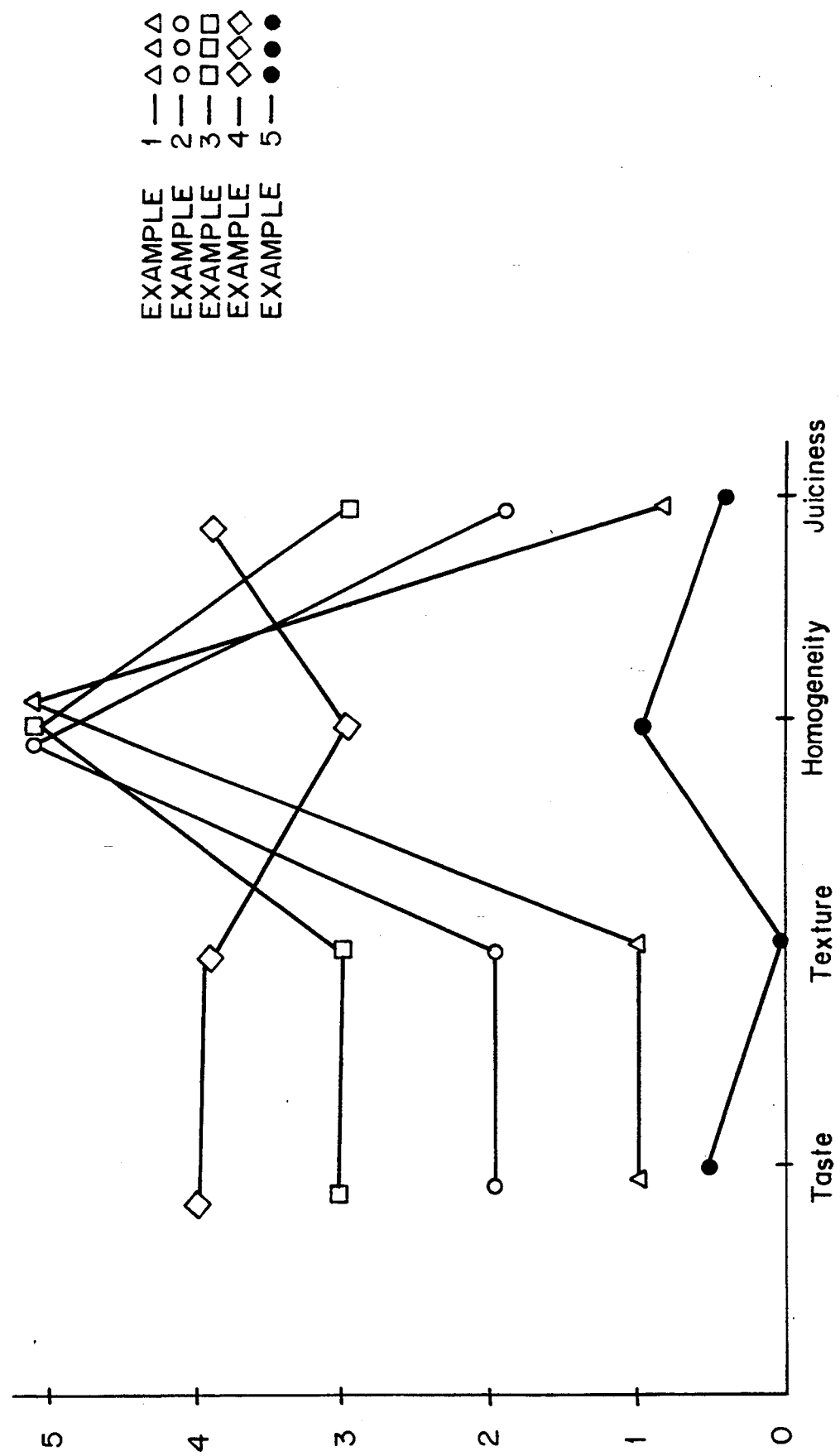
FIG. 1 is a graph which depicts the results of data collected from comparative testing conducted to demonstrate the efficacy of the present invention.

The present invention concerns the use of starch as a key ingredient in the formation of food products and as an ingredient for enhancing food products. In the present invention a matrix which is formed by flash-flow processing can be combined with starch and added to a food product, especially a protein-based food product, in order to enhance the gustatory qualities thereof.

The present invention also includes the use of additional components in the food enhancing ingredient and the food products. In particular, an oleaginous substance can be combined with the carrier material, or the oleaginous substance can be combined with the carrier and/or starch prior to being subjected to flash-flow processing. The oleaginous substance can be selected from the group consisting of animal fats, such as tallows and lards, fish oils and crustacean oils, vegetable oils, and mixtures thereof.

In one preferred embodiment, the carrier is corn syrup solids (a maltodextrin), and the resulting matrix is in the form of flakes. Surprisingly, it has been found that the flake form inhibits microbial growth, and possibly has a bactericidal effect in food products.

While applicant is not bound by theory, it appears that maltodextrins have an antioxidant and bactericidal effect on edible proteins when incorporated therein. The extended shelf-life is observed in ground meats such as ground chicken, ground turkey, and ground beef and is especially advantageous property when the bulk protein material has low salt levels. Consequently, growth of microorganisms such as *E. Coli*; choliform, et al. is controlled.

Moreover, water can be added to and retained in meat products which have been prepared in accordance with the present invention. This is contrary to conventional practice in ground meat art. The result, however, is quite beneficial in that juiciness seems to be enhanced, and the meat appears to be steamed during cooking.

Another ingredient which has been found to be quite useful in the present invention is oleoresin. Oleoresin is a natural combination of resins and essential oils exuded from plants. Oleoresin extract includes the flavoring components of the spice which are soluble in the solvent used in the extraction process. Flavor is due to both volatile and nonvolatile components in herbs and spices. Most constituents are hydrophobic and, consequently, are extracted with nonpolar solvents such as hydrocarbons. Other flavor components are hydrophilic, and require recovery with a polar solvent such as acetone. Water has also been used as a solvent to produce stable spice extracts of a fresh herb or spice, and is carried out on frozen comminuted material which has been treated with acetic acid before hydraulic expression.

Oleoresin as used herein also includes water/oil-dispersable oleoresins. Water/oil-dispersable spice oleoresins can be obtained from Kalsec ® Inc. of Kalamazoo, Mich. under the trademark AQUARESIN ®. Kalsec ® Inc. claims such resins are covered by one or more of U.S. Pat. Nos. 4,283,429; 4,315,947; 4,285,981; and 4,343,823.

Oleoresins can deliver spices such as tarragon, thyme, sage, rosemary, oregano, nutmeg, basil, bay, cardamom flavor, celery (including sweet celery), cilantro, cinnamon, clove, coriander, cumin, fennel, ginger, mace, marjoram, capsicum, black pepper, white pepper, annatto, paprika, turmeric, cajun, and mixtures thereof including allspice. The present invention also contemplates the use of spice, such as those set forth above. The oleoresins can be used in the enhanced food ingredient or in the products prepared herewith. Thus, the oleoresin or spice can be combined with the carrier material prior to being subjected to flash-flow conditions. In food products, the spice or oleoresin can also be incorporated in the food product as an ingredient separate from the matrix.

The present invention can also include a flavor oil such as peppermint oil, spearmint oil, cinnamon oil, oil of wintergreen, nut oil, licorice, vanilla, citrus oils, fruit essences and mixtures thereof. Citrus oils and fruit essences can be selected from apple, apricot, banana, blueberry, cherry, coconut, grape, grapefruit, lemon, lime, orange, pear, peaches, pineapple, plum, raspberry, strawberry, and mixtures thereof.

The carrier material of the present invention can be saccharide, cellulosics and mixtures thereof. A saccharide can be any one of, for example, sucrose, lactose, fructose, dextrose, sorbitol, mannitol, maltitol, maltose, polydextrose, maltodextrins, oligosaccharides derived from chicory root, and mixtures thereof. The maltodextrin feed stock of the present invention is a saccharide based solid material consisting of nonsweet, nutritive saccharide polymers and other glucose bearing oligomers as well as glucose units, which collectively provide a carrier material capable of forming a matrix. The Dextrose Equivalent (D.E.) of the maltodextrin feedstock is less than forty (40). In a preferred embodiment of the present invention the D.E. can be between twenty (20) and forty (40), and yet another preferred embodiment the D.E. can be between ten (10) and twenty (20). Preferably, the maltodextrin used as a carrier in the present invention is deionized. However, ionized maltodextrins can be used also.

The present invention also includes starch as a basic component. Starch is a carbohydrate or polysaccharide which is derived from plant cells. Starch basically includes two fractions, amylose which is a substantially straight chain polysaccharide and amylopectin which is a branched form of the polysaccharide. Generally speaking, starches contain up to about 32% amylose while the remainder is substantially amylopectin.

In a preferred embodiment, waxy starch is used in the present invention. Waxy starch is defined as a starch which has an amylose content of not more than about 20%, and in a most preferred embodiment not greater than about 17%. Waxy starches can be derived from, for example, tapioca.

The starches of the present invention can be modified or unmodified starches. Starches can be modified by acid treatment, bleaching, oxidizing, esterified, etherified, or modified with treatment by, for example, alpha-amylase, chlorine, and sodium hydroxide. The starch may also be modified by a combination of treatments set forth above. One food modified starch which can be used in the present invention is sold by National Starch and Chemical Co. of Bridgewater, N.J. and is known by the trade name LEANBIND TM, which has an amylose content of less than 20%

The present invention has been found to be particularly useful in protein based food products and includes both the food enhancing ingredient as well as the food product itself. Protein based food products may have a source of protein which is derived from meat products, soy, vegetables, and can be in the form of, for example, ground meat products. Thus, such products can include hamburger products, turkey or seafood-based products, soy-based or vegetable-based products in the form of patties, steaks, and fillets.

The matrix is provided in the present invention by subjecting the carrier and any other materials previously combined therewith to a flash-flow process. "Flash-flow" is referred to in the present invention as a phenomena which occurs when a solid carrier material is subjected to conditions of temperature and shear sufficient to provide internal flow at a subparticle level. This condition produces a transformation of physical and/or chemical structure without degradation of the material. Internal flow occurs when the infrastructure of the material breaks down sufficiently to permit movement of the material at a subparticle level, and probably at a molecular level. At a molecular level, internal flow contemplates the movement of molecules relative to each other. Flash-flow can be achieved by spinning the carrier material in a high speed spinner which has a spinning head having a conductive heat element on the perimeter thereof. This apparatus is similar to "cotton candy" type machine. The spinning machine used to achieve flash flow processing can be a cotton candy type machine, such as the Econo-Floss Model 3017 manufactured by Goldmetal Products Company of Cincinnati, Ohio.

Another method of producing flash-flow is by a shearform process such as that disclosed in commonly owned U.S. application Ser. No. 965,804, now U.S. Pat. No. 5,380,473. The contents of U.S. Pat. No. 5,380,473 are incorporated herein by reference.

The matrix obtained in the flash heat process is in the form of a floss, fiber, particle, flake, spicule, or any other generally nondescript amorphous aggregate. As a result of the unique combination of the matrix material and the starch, it has been found that the texture cohesiveness, and moisture retention of food products are significantly enhanced. This appears to be the case from experimentation even when the same starch product is used alone in the protein based food product.

It is also contemplated that food gums, such as carageenen, xanthan, and other gums can be included in the feedstock and processed to form the matrix of the present invention.

Suitable cellulosic materials include methyl cellulose, ethyl cellulose, hydroxyethylcellulose, alkali-metal salts of carboxymethylcelluloses and the like and mixtures thereof.

The starch and matrix combination as well as the starch bearing matrix are especially well suited for products containing at least 60% edible protein. Such products include meat products, fish, crustacean based and/or protein based compositions such as soy or vegetable products. Meats can include beef, pork, lamb, chicken, turkey, horse meat, and the like and mixtures thereof to provide a wide array of enhanced products. In addition the matrix may be combined with protein material such as soy or vegetable based products. Examples of such products include soy, soy burger additives or vegetable byproducts.

It is also contemplated that the invention can be used with most processed meat products, especially those which normally include a substantial level of fat in order to obtain desired taste characteristics. For example hot dogs, sausages, wursts, beef jerky, pet foods and the like may be prepared in accordance with the present invention.

In one embodiment, it has been found that exceptionally tasty meat products can be prepared by exchanging a portion (or all) of the fat found in the meat or protein based product with the matrix and starch compositions of the present invention. Even when oleaginous material is included in the matrix, the overall content of the fat can be significantly reduced. For example, a typical beef hamburger product can be prepared which has as low as about 5% percent of overall fat, without losing the gustatory qualities of a 20%–30% fat-containing burger.

Additional advantages include an extension of shelf life of the food products which contains the inventive combination, and the high efficiency in producing protein based products with presently available equipment.

Ancillary additives include other edible ingredients such as preservatives, colorants, dyes and so forth. It has been found that by using the present invention, cooked protein products retain the taste and texture as well as the juiciness of the product. Thus, the consumer will readily select the lower fat containing product because of its comparable destitory qualities.

Examples have been set forth herein which demonstrate the efficacy of the present invention. These examples are provided to show the present preferred embodiments and to explain the unique qualities of products prepared with the present invention, but are not intended to, in any way, limit the scope of the present invention.

EXAMPLES OF THE INVENTION

Three matrices were prepared in order to be tested with protein-based food product. The first matrix included 80% maltodextrin having a D.E. of 36 (Hubinger Dri Sweet 36), and 20% cannola oil. The combination was spun in a spinning apparatus to provide a white flake aggregate.

A second matrix material was prepared which consisted of 91% maltodextrin having a D.E. of 36 and 9% oleaginous. The ingredients were mixed and subjected to high speed spinning for two minutes to produce results similar to that set forth in B except that the flakes were somewhat smaller.

A third matrix was prepared which included 71% maltodextrin having a D.E. of 36, 9% oleaginous material (Canola Oil) in the way of canola oil, and 20% food modified starch sold by the National Starch and Chemical Company under the trademark LEANBIND TM. The ingredients were mixed as in matrix A and subjected to spinning in the same high speed spinning machine for two minutes. White flakes were produced after the process reached steady state.

The compositions for each of the three matrix materials have been set forth in summary fashion in Table 1.

TABLE 1

| INGREDIENT | MATRIX A | MATRIX B | MATRIX C |
| --- | --- | --- | --- |
| Maltodextrin D.E.36 | 80% | 91% | 71% |
| Oleaginous | 20% | 9% | 9% |
| Starch | — | — | 20% |

These matrices were used in the examples set forth below to compare protein based food products without the inventive compositions.

It has been found from experimentation that a high quality matrix can be prepared with excellent yield, e.g., 85% to 95%, by processing corn syrup solids, a maltodextrin, LEANBIND TM starch and canola oil in a high speed spinning machine at a speed of about 3,600 r.p.m. A working range is from about 3,500 r.p.m. to about 3,700 r.p.m., and a preferred range is from about 3,550 r.p.m. to about 3,650 r.p.m. The temperature used to process the material was 135° C. A working temperature range for processing the maltodextrin/canola oil/starch feedstock is from about 130° C. to about 140° C. with a preferred range from about 130° C. to about 138° C.

EXAMPLE ONE

Four different hamburger products were prepared in order to compare the results using the present invention with a low fat, high quality hamburger food product. A control example was prepared using 100 grams of 90% fat free ground beef. The 100% ground beef patty was cooked on a hot plate at 350 degrees for two minutes per side. The resulting hamburger was subjected to a taste test with a five member panel. The panel members tested four primary qualities of the product: taste, texture, juiciness, and product homogeneity (i.e., consistency of the product throughout the patty). The 100% ground beef patty was used as the standard against which examples 2, 3 and 4 were compared. The results of the test have been set forth below after a description of each of the example patties.

EXAMPLE TWO

A second example was prepared which included 89.5% ground beef, 8% added water and 2.5% of matrix A. Thus, example 2 is a product prepared in accordance with parent U.S. Pat. No. 5,387,431.

All of the compositions used in the examples have been set forth in table 2 herein below.

The sample of example two was formed into a 100 gram patty which was cooked at 350° on a hot plate for two minutes on each side. The sample was submitted to the five member test panel for determining the quality of taste, texture, homogeneity and juiciness or moisture retention.

EXAMPLE THREE

In example three, a composition was prepared which included 89.5% ground beef, 8% added water and 2.5% of matrix C. Thus, example 3 is a manifestation of the present invention wherein the starch material is incorporated in the matrix.

The composition was formed into a 100 gram patty and cooked two minutes on each side on a hot plate at 350° F. The taste tests were conducted on the example three and compared to the other examples set forth herein. For comparison of the compositions in accordance with the examples see table two here and below.

EXAMPLE FOUR

A fourth sample was prepared which incorporated 89.5% ground beef, 8% added water, 2% of matrix B and 0.5% of modified food starch sold under the trademark LEANBIND TM. Thus, the composition of example four shows the use of the matrix material and the starch as a combination in the protein-based product, but the starch was not subjected to flash-flow processing and made part of the matrix.

The composition was formed into a 100 gram patty and cooked on a hot plate at 350° F. for two minutes on each side. Taste tests to determine the comparative taste, texture, homogeneity and juiciness was made by the five member taste panel.

TABLE 2

| INGREDIENTS | EXAMPLES | | | |
| --- | --- | --- | --- | --- |
| | 1 | 2 | 3 | 4 |
| Ground Beef 90% Fat Free | 100% | 89.5% | 89.5% | 89.5% |
| Added | — | 8.0% | 8.0% | 8.0% |

TABLE 2-continued

| INGREDIENTS | EXAMPLES | | | |
|---|---|---|---|---|
| | 1 | 2 | 3 | 4 |
| Water | | | | |
| Starch | — | — | — | 0.5% |
| Matrix A | — | 2.5% | — | — |
| Matrix B | — | — | — | 2.0% |
| Matrix C | — | — | 2.5% | — |

The products prepared were submitted to the test panel in a blind test. Thus, the tasters did not know the origin or composition of any of the samples which they tasted.

Upon analysis of the comparative examples set forth below, it can be seen that the low fat hamburger by itself, Example 1, was the least desired—the rating was the lowest of all the samples. Example 2 which basically sets forth the previous invention of the parent application showed an improvement over the low fat hamburger patty.

TABLE 3

| QUALITY | EXAMPLES OF THE INVENTION | | | |
|---|---|---|---|---|
| | 1 | 2 | 3 | 4 |
| Taste | + | ++ | +++ | ++++ |
| Homogeneity Product | +++++ | +++++ | +++++ | +++ |
| Texture | + | ++ | +++ | ++++ |
| Juiciness | + | ++ | +++ | ++++ |

However Examples 3 and 4 which included the starch in the matrix itself and then in the composition (outside the matrix), respectively, were far superior to Example 1 and Example 2 with respect to taste, texture and juiciness. The homogeneity or product consistency for Example 4, however, was not as highly rated as in Examples 2 and 3. (The homogeneity of Example 1 by definition must have the highest rating since it was not mixed with any other components). The test panel determined that the products of Examples 3 and 4 were both of high quality, and both were superior to Example 2.

It is noted that for large volume manufacturing Example 3 is the most desirable since all of the essential ingredients are contained in the matrix delivery system thereby significantly streamlining the processing procedures.

EXAMPLE FIVE

Finally, another control example was prepared in which the recommended amount of LEANBIND TM, e.g. 1.0%–1.5%, was used in combination with low fat ground beef (90% fat free) without starch. Example 5 was prepared to test the starch and matrix in a protein based product as defined herein. The product was prepared by mixing the LEANBIND TM starch and ground beef, and then formed into a 100 gram patty which was cooked at 350° F. on a hot plate for two minutes on each side. The product was tasted by independent tasters and awarded nominal ratings of taste, texture, juiciness, and homogeneity. The comments with respect to the low fat beef patty with starch alone were as follows.

With respect to taste, the testers indicated that the taste was a waxy flavor having a tapioca note which overpowered the beef flavor. They indicated that the taste was unacceptable for a beef patty product.

With respect to texture, the testers indicated that the texture was mushy having an overly-soft-continuum feeling in the mouth which did not permit crisp detachment usually associated with maceration of a beef patty.

With respect to moisture retention, the testers noted that the product had an overall soggy appearance and presentation to the mouth. The moisture which was retained gave the impression of dissolving the base product both in appearance and gustatory qualities.

Finally with respect to homogeneity, the tasters described the product as discontinuous based on, among other things, the moisture separating from the patty.

The tasters were unanimous in their assessment that the product prepared with starch plus the matrix material (as well as starch incorporated in the matrix material) was vastly superior to the LEANBIND TM product in combination with the low beef patty. They also assessed Examples 1 and 2 with the LEANBIND TM patty and rated Examples 1 and 2 superior to the product in which ground beef was combined with starch by itself.

The results of those tests have been entered in graph format in FIG. 1 in order to depict the dramatic results achieved using the present invention. It is of particular interest that the inventive compositions of Example 3 and the previous invention of Example 2 achieved the same degree of product homogeneity as the beef-only example!

OLEORESIN EXAMPLES

An equally dramatic showing of the efficacy of the present invention pertains to enabling the artisan to incorporate intense-flavored oleoresins into a protein-based food product such as ground meat, e.g., ground beef and ground turkey. Oleoresins by their very nature are high intensity flavorants. Consequently, it is very difficult to use oleoresins in food products which are bulky. This is especially true of protein-based food products such as soy burgers, hamburgers, turkey burgers, etc. In fact, it has been found that it is quite difficult to obtain a uniform distribution of oleoresins by mixing in ground meat products.

EXAMPLE SIX

Once again, ground beef product (which is 90% fat free) was provided for mixing with an oleoresin. The oleoresin was mixed by use of a standard mixing apparatus. Oleoresin was gradually added to the ground beef during mixing in a Hobart mixer at a ratio of 0.075 oz. of oleoresin to 50 ounces of ground beef. The mixing apparatus was permited to continue until a thorough mixture of the oleoresin was provided in the ground beef. When the oleoresin was finally thoroughly combined with the ground beef, the texture of the meat had deteriorated so greatly that it had become pasty and generally undesirable for cooking and consumption.

The same procedure was conducted using ground turkey as the source of protein. Once again the oleoresin was gradually added during mixing in a Hobart mixer in an amount of 0.075 oz. of oleoresin to 50 ounces of ground turkey. A standard mixing apparatus was used to combine the two ingredients. Before the oleoresin was completely mixed with the ground turkey, the texture of the meat had thoroughly deteriorated, thus making it undesirable for cooking and consumption.

These examples are to be compared with Example 7 which employed the present invention to effect mixing of high intensity oleoresin flavors.

EXAMPLE SEVEN

A feedstock was prepared in accordance with the formula set forth in Table 4.

TABLE 4

| INGREDIENTS | AMOUNT | % |
|---|---|---|
| Oleoresin (Cajun AQUARESIN ®) | 1.5 lbs. | 3% |
| Oleaginous Material (Canola Oil) | 1.5 lbs. | 5% |
| Starch (LEANBIND ™) | 10 lbs. | 20% |
| Carrier (DriSweet 36 ™) | 36 lbs. | 72% |
| | 50 lbs. | 100% |

The feedstock was delivered to a flash-flow process provided by a high speed spinning machine (at 3600 r.p.m.) It was run at temperature of about 130° C. for a time period of about 12 minutes. The spinning procedure provided a consistent flake ideal for combining with hamburger.

Next the material was introduced to the same standard mixing apparatus which was used in Example 6 at a rate of 1.25 ounces amount matrix to 45 ounces of ground beef. The product was stirred very easily in a Hobart mixer at high speed for only about 30 seconds. The resultant composition was a thoroughly mixed protein product having the matrix combined throughout. Four (4) ounces of water was then added while the mixture was mixed in the Hobart mixer for another 10 seconds to obtain a uniform mix.

Consequently, the product contained spice oleoresin thoroughly mixed in the ground beef without any unwanted "hot spots". The product also had excellent texture and bulk for cooking and consumption. Patties were formed at sizes of 100 gms. and cooked on a hot plate at 350° F. for two minutes on each side. Use of the unique "matrix-plus-starch" combination of the present invention enable the investigators to prepare a highly desirable meat patty which cooked nicely to a spiced hamburger product.

Thus, while there had been described what are presently believed to be the preferred embodiments of the present invention, those skilled in the art will appreciate that further modifications can be made to the invention without departing from the true scope thereof, and it is intended to include all such modifications within the claims as set forth here and below.

I claim:

1. A food enhancing ingredient comprising:
   a matrix formed by subjecting a carrier material to flash-flow processing, wherein internal flow is provided thereby permittinq transformation of structure without degradation of said carrier material, and a waxy starch having an amylose content of not greater than about 20% mixed with said matrix.

2. The food enhancing ingredient of claim 1 wherein said waxy starch is included in an amount of not more than about 35% of said ingredient.

3. The food enhancing ingredient of claim 2 wherein said waxy starch is present in an amount of not more than about 25% of said ingredient.

4. The food enhancing ingredient of claim 1 wherein said matrix further comprises an oleaginous substance combined with said carrier material prior to being subjected to said flash-flow processing.

5. The food enhancing ingredient of claim 4 wherein said oleaginous substance is selected from the group consisting of animal fats, tallows, lards, fish oils, crustacean oils, vegetable oils and mixtures thereof.

6. The food enhancing ingredient of claim 1 wherein said matrix further comprises an oleoresin combined with said carrier material prior to being subjected to flash-flow processing.

7. The food enhancing ingredient of claim 1 wherein said matrix further comprises a spice combined with said carrier material prior to being subjected to flash-flow processing.

8. The food enhancing ingredient of claim 1 wherein said matrix further comprises a flavor oil combined with said carrier material prior to being subjected to flash-flow processing.

9. The food enhancing ingredient of claim 1 wherein said amylose content is not greater than 17%.

10. The food enhancing ingredient of claim 1 wherein said carrier material is selected from the group consisting of saccharides, cellulosic material and mixtures thereof.

11. The food enhancing ingredient of claim 10 wherein said carrier material is a saccharide selected from the group consisting of sucrose, lactose, fructose, dextrose, sorbitol, mannitol, maltose, polydextrose, and maltodextrins, and mixtures thereof.

12. The food enhancing ingredient of claim 11 wherein said saccharide is deionized maltodextrin.

13. The food enhancing ingredient of claim 10 wherein said carrier material is a cellulosic material selected from the group consisting of methyl cellulose, ethyl cellulose, hydroxymethylcellulose, hydroxyethylcellulose, alkali-metal salts of carboxymethylcellulose and mixtures thereof.

14. The food enhancing ingredient of claim 1 wherein said matrix is in the form of flakes which exhibit a bactericidal effect in food.

15. A comestible matrix comprising:
    a combination of a carrier and a waxy starch having an amylose content of not greater than about 20% prepared by the process of subjecting a mixture of said carrier and said waxy starch to flash-flow processing, wherein internal flow is provided thereby permitting a transformation of structure without degradation of said mixture.

16. The matrix of claim 15 wherein said waxy starch is combined with said carrier in an amount of not more than about 35% by weight of said combination.

17. The matrix of claim 16 wherein said waxy starch is combined in an amount of not more than about 25% weight of said combination.

18. The matrix of claim 16 wherein said carrier is a saccharide selected from the group consisting of sucrose, lactose, fructose, dextrose, sorbitol, mannitol, maltose, polydextrose, maltodextrin, and mixtures thereof.

19. The matrix of claim 15 wherein said carrier is selected from the group consisting of saccharides, cellulosic materials and mixtures thereof.

20. The matrix of claim 19 wherein said carrier is deionized maltodextrin.

21. The matrix of claim 19 wherein said carrier is a cellulosic material selected from the group consisting of methyl cellulose, ethyl cellulose, hydroxymethylcellulose, hydroxyethylcellulose, alkali-metal salts of carboxymethylcellulose and mixtures thereof.

22. The matrix of claim 15 wherein said amylose content is not greater than about 17%.

23. The matrix of claim 15 which further comprises an oleaginous material combined with said carrier and said waxy starch prior to being subjected to flash-flow processing.

24. The matrix of claim 23 wherein said oleaginous material is selected from the group consisting of animal fats, tallows, lards, fish oils, crustacean oils, vegetable oils, soy-based products, and mixtures thereof.

25. The matrix of claim 15 which further comprises a flavor oil combined with said carrier and said waxy starch prior to said carrier and said waxy starch being subjected to flash-flow processing.

26. The matrix of claim 15 which further comprises an oleoresin combined with said carrier and said waxy starch prior to said carrier and said waxy starch being subjected to flash-flow processing.

27. The matrix of claim 15 which further comprises a spice combined with said carrier and said waxy starch prior to said carrier and said waxy starch being subjected to flash-flow processing.

28. The matrix of claim 15 which is in the form of flakes which exhibit a bactericidal effect in food.

* * * * *